(12) United States Patent
Ostgard et al.

(10) Patent No.: US 8,889,911 B2
(45) Date of Patent: Nov. 18, 2014

(54) ACTIVATED BASE METAL CATALYSTS

(75) Inventors: Daniel Ostgard, Kleinostheim (DE);
Monika Berweiler, Maintal (DE);
Markus Göttlinger, Rodenbach (DE);
Steffen Laporte, Rodgau (DE);
Matthias Schwarz, Flieden (DE)

(73) Assignee: Evonik Degussa GmbH, Essen (DE)

( * ) Notice: Subject to any disclaimer, the term of this patent is extended or adjusted under 35 U.S.C. 154(b) by 885 days.

(21) Appl. No.: 12/601,820

(22) PCT Filed: May 29, 2007

(86) PCT No.: PCT/EP2007/055186
§ 371 (c)(1),
(2), (4) Date: Nov. 24, 2009

(87) PCT Pub. No.: WO2008/145181
PCT Pub. Date: Dec. 4, 2008

(65) Prior Publication Data
US 2010/0174116 A1    Jul. 8, 2010

(51) Int. Cl.
*C07C 209/00* (2006.01)
*B01J 25/02* (2006.01)
*C07C 209/36* (2006.01)

(52) U.S. Cl.
CPC ............... *B01J 25/02* (2013.01); *C07C 209/36* (2013.01)
USPC ........................................................ 564/421

(58) Field of Classification Search
None
See application file for complete search history.

(56) References Cited

U.S. PATENT DOCUMENTS

| 2,619,503 A | 11/1952 | Benner et al. |
| 2,823,235 A | 2/1958 | Graham et al. |
| 3,127,356 A | 3/1964 | Hamilton et al. |
| 3,328,465 A | 6/1967 | Spiegler |

(Continued)

FOREIGN PATENT DOCUMENTS

| DE | 21 59 736 | 6/1973 |
| EP | 0 437 788 A1 | 7/1991 |

(Continued)

OTHER PUBLICATIONS

H. Lei et al. Applied Catalysis A: General 214 (2001) 69-76.*

(Continued)

*Primary Examiner* — Clinton Brooks
(74) *Attorney, Agent, or Firm* — Law Office of: Michael A. Sanzo, LLC

(57) ABSTRACT

Nitro-compounds are hydrogenated with an activated Ni catalyst that is doped during and/or after activation with one or more elements from the list of Mg, Ca, Ba, Ti, Zr, Ce, Nb, Cr, Mo, W, Mn, Re, Fe, Co, Ir, Ni, Cu, Ag, Au, Rh, Ru and Bi whereas the Ni/Al alloy may not, but preferentially can contain prior to activation one or more doping elements from the list of Ti, Ce, V, Cr, Mo, W, Mn, Re, Fe, Ru, Co, Rh, Ir, Pd, Pt and Bi. If the Ni/Al alloy contained one or more of the above mentioned suitable alloy doping elements prior to activation, the resulting catalyst can then be doped with one or more of the elements from the list of Mg, Ca, Ba, Ti, Zr, Ce, V, Nb, Cr, Mo, W, Mn, Re, Fe, Ru, Co, Rh, Ir, Ni, Pd, Pt, Cu, Ag, Au and Bi by their adsorption onto the surface of the catalyst.

20 Claims, 2 Drawing Sheets

Graph 1.  The DNT pulse hydrogenation data for CE1, CE2, CE3, E1 and E2.

(56) References Cited

U.S. PATENT DOCUMENTS

| | | | |
|---|---|---|---|
| 3,839,011 A | | 10/1974 | Larson, Jr. |
| 3,997,478 A | * | 12/1976 | Petro .............................. 502/301 |
| 4,153,578 A | | 5/1979 | De Thomas et al. |
| 4,182,721 A | | 1/1980 | De Thomas et al. |
| 4,224,249 A | | 9/1980 | Kunz et al. |
| 4,720,346 A | | 1/1988 | Flesher et al. |
| 4,792,626 A | | 12/1988 | Becher et al. |
| 4,978,649 A | | 12/1990 | Surovikin et al. |
| 5,051,164 A | | 9/1991 | Herbst et al. |
| 5,090,997 A | | 2/1992 | Birkenstock et al. |
| 5,238,663 A | | 8/1993 | Vikari et al. |
| 5,554,573 A | | 9/1996 | Cordier et al. |
| 6,005,143 A | | 12/1999 | Machado et al. |
| 6,309,758 B1 | | 10/2001 | Schmidt |
| 6,395,403 B2 | | 5/2002 | Schmidt |
| 6,423,872 B2 | | 7/2002 | Marion |
| 6,429,337 B1 | | 8/2002 | Schmidt |
| 2001/0027257 A1 | | 10/2001 | Marion |
| 2002/0173676 A1 | * | 11/2002 | Ostgard et al. ................. 564/490 |
| 2005/0043566 A1 | | 2/2005 | Morgenstern et al. |
| 2005/0107251 A1 | | 5/2005 | Zechlin et al. |
| 2008/0154061 A1 | * | 6/2008 | Ernst et al. ..................... 564/372 |
| 2008/0182745 A1 | | 7/2008 | Finkelshtain et al. |
| 2009/0264679 A1 | | 10/2009 | Ostgard et al. |
| 2010/0185026 A1 | | 7/2010 | Ostgard et al. |
| 2010/0204517 A1 | * | 8/2010 | Ostgard et al. ................. 564/421 |
| 2010/0249460 A1 | | 9/2010 | Ostgard et al. |

FOREIGN PATENT DOCUMENTS

| | | | |
|---|---|---|---|
| GB | 904 117 | 8/1962 | |
| GB | 1 401 673 | 7/1975 | |
| JP | 62-99350 | 5/1992 | |
| JP | 4-214807 | 8/1992 | |
| JP | 55-15692 | 2/2002 | |
| JP | 2002-543963 | 12/2002 | |
| JP | 2004-71070 | 3/2004 | |
| WO | WO 00/67903 | 11/2000 | |
| WO | WO2006089931 | * 8/2006 | ............ C07C 209/48 |
| WO | WO 2006/134403 A2 | 12/2006 | |
| WO | WO 2007/028411 A1 | 3/2007 | |
| WO | WO 2008/145179 A1 | 12/2008 | |
| WO | WO 2008/145180 A1 | 12/2008 | |
| WO | WO 2009/049662 A1 | 4/2009 | |

OTHER PUBLICATIONS

Neri, et al., "Kinetic Modeling of 2,4-Dinitroluene Hydrogenation over Pd/C," *Ind. Eng. Chem. Res.* 34:2226-2231 (1995).
Restriction Requirement for co-pending U.S. Appl. No. 12/682,080, mailed Mar. 28, 2012.
Response to Restriction Requirement for co-pending U.S. Appl. No. 12/682,080, filed May 26, 2012.
Restriction Requirement for co-pending U.S. Appl. No. 12/601,815, mailed May 23, 2012.
Response to Restriction Requirement for co-pending U.S. Appl. No. 12/601,815, filed Jun. 16, 2012.
Amendment to Accompany Response to Restriction Requirement for co-pending U.S. Appl. No. 12/601,815, filed Jun. 16, 2012.
Response to Office Action filed Jan. 14, 2013 for co-pending U.S. Appl. No. 12/601,815.
Office Action mailed Jan. 16, 2013 for co-pending U.S. Appl. No. 12/601,816.
International Search Report for PCT/EP2007/055186 filed May 29, 2007.
Written Opinion of the International Searching Authority for PCT/EP2007/055186 filed May 29, 2007.
International Preliminary Report on Patentability for PCT/EP2007/055186 filed May 29, 2007.
English language abstract for German patent document DE 21 59 736, listed as document B1 above, Jun. 14, 1973.
English language translation of Taiwan Office Action for co-pending U.S. Appl. No. 12/601,815, Mar. 28, 2012.
English language translation of Taiwan Office Action for U.S. Appl. No. 12/601,820, Mar. 28, 2012.
Restriction Requirement for co-pending U.S. Appl. No. 12/601,816, mailed Jan. 27, 2012.
Response to Restriction Requirement for co-pending U.S. Appl. No. 12/601,816, filed Mar. 26, 2012.
International Preliminary Examination Report for PCT/EP2007/055186 (international stage of U.S. Appl. No. 12/601,820), Jan. 12, 2009.
International Preliminary Examination Report for PCT/EP2007/055184 (international stage of U.S. Appl. No. 12/601,815), Jan. 12, 2009.
Preliminary Amendment filed by Applicants in copending U.S. Appl. No. 12/601,815 on Nov. 24, 2009.
International Preliminary Examination Report for PCT/EP2007/055185 (international stage of U.S. Appl. No. 12/601,816), Jan. 12, 2009.
Preliminary Amendment filed by Applicants in copending U.S. Appl. No. 12/601,816 on Nov. 24, 2009.
International Preliminary Examination Report for PCT/EP2007/060942 (international stage of U.S. Appl. No. 12/682,080), Apr. 20, 2010.
Preliminary Amendment filed by Applicants in copending U.S. Appl. No. 12/682,080 on Apr. 8, 2010.
English translation of Office Action in Chinese application 200780053152.6 (Chinese counterpart of U.S. Appl. No. 12/601,816), Nov. 13, 2011.
English translation of Office Action in Chinese application 200780053154.5 (Chinese counterpart of U.S. Appl. No. 12/601,820), Nov. 13, 2011.
English language abstract for JP 2004-71070 listed as document B1 above, Mar. 12, 2004.
Augustine, R.L., "Unsupported Metals," Heterogeneous catalysis for the synthetic chemist, Chapter 12, pp. 229-265, Marcel Dekker, Inc., New York, NY (1996).
Chan, et al., "Materials Science and Technology," Processing of Metals and Alloys, pp. 57-110, vol. 15, VCH-Verlag Weinheim, Germany (1991).
Office Action for co-pending U.S. Appl. No. 12/682,080, mailed Aug. 3, 2012.
Office Action for co-pending U.S. Appl. No. 12/601,816, mailed Jul. 9, 2012.
Response to Office Action filed Sep. 4, 2012 for co-pending U.S. Appl. No. 12/601,816.
Office Action for co-pending U.S. Appl. No. 12/601,815, mailed Oct. 15, 2012.
Response to Office Action filed Nov. 3, 2012 for co-pending U.S. Appl. No. 12/682,080.
Hofer, et al., "Correlation between the Catalytic Activity of Raney Nickel and its Structure," *Transactions of the Faraday Society* 60:1457-1465 (1964).
English language abstract for JP 62-99350, listed as document B1 above, May 8, 1992.
English language abstract for JP 4-214807, listed as document B2 above, Aug. 5, 1992.
English language abstract for JP 55-15692, listed as document B3 above, Feb. 2, 2002.
English language abstract for JP 2002-543963, listed as document B4 above, Dec. 24, 2002.
Translation of Office Action for counterpart Japanese patent application No. JP 2010-50692, Nov. 19, 2002.
Translation of Japanese Office Action for counterpart of copending U.S. Appl. No. 12/601,816, Nov. 19, 2002.
RCE and Amendment for U.S. Appl. No. 12/601,815, filed Apr. 23, 2014.
Response to Office Action of Mar. 12, 2014 for U.S. Appl. No. 12/601,816 filed Jun. 18, 2014.
Office Action for co-pending application U.S. Appl. No. 12/682,080, mailed Feb. 27, 2013.
Response to Office Action of Feb. 27, 2013 for U.S. Appl. No. 12/682,080, filed Jul. 18, 2013.
Advisory Action for U.S. Appl. No. 12/682,080, mailed Aug. 15, 2013.

(56) References Cited

OTHER PUBLICATIONS

RCE for U.S. Appl. No. 12/682,080, filed Oct. 2, 2013.
Response to Office Action for co-pending application U.S. Appl. No. 12/601,816, filed on Apr. 13, 2013.
Office Action for co-pending application U.S. Appl. No. 12/601,816 mailed Sep. 23, 2013.
Response to Office Action of Sep. 23, 2013 for U.S. Appl. No. 12/601,816 filed Dec. 10, 2013.
Office Action for copending application U.S. Appl. No. 12/601,816 mailed Mar. 12, 2014.
Office Action for copending application U.S. Appl. No. 12/601,815, mailed May 23, 2013.
Response to Office Action of May 23, 2013 for U.S. Appl. No. 12/601,815, filed Aug. 23, 2013.
Advisory Action for U.S. Appl. No. 12/601,815, mailed Sep. 16, 2013.
Appeal Brief for U.S. Appl. No. 12/601,815, filed Oct. 24, 2013.
Notice of Allowance for U.S. Appl. No. 12/601,815, mailed Feb. 20, 2014.

* cited by examiner

Graph 1. The DNT pulse hydrogenation data for CE1, CE2, CE3, E1 and E2.

Graph 2. The DNT pulse hydrogenation data for CE1, CE2, CE3, E3, E4, E5, E6 and E7.

ACTIVATED BASE METAL CATALYSTS

CROSS REFERENCE TO RELATED APPLICATIONS

The present application is US national stage of international application PCT/EP2007/055186, which had an international filing date of May 29, 2007, and which was published in English under PCT Article 21(2) on Dec. 4, 2008.

The invention concerns an activated base metal catalyst, and its use for the hydrogenation of nitro-compounds.

Activated metal catalysts are also known in the fields of chemistry and chemical engineering as Raney-type, sponge and/or skeletal catalysts. They are used, largely in powder form, for a large number of hydrogenation, dehydrogenation, isomerization, reductive amination, reductive alkylation and hydration reactions of organic compounds. These powdered catalysts are prepared from an alloy of one or more catalytically-active metals, also referred to herein as the catalyst metals, with a further alloying component which is soluble in alkalis. Mainly nickel, cobalt, copper, iron or combinations thereof are used as catalyst metals. Aluminum is generally used as the alloying component which is soluble in alkalis, but other components may also be used, in particular zinc and silicon or mixtures of these either with or without aluminum.

These so-called Raney alloys are generally prepared by the ingot casting process. In that process a mixture of the catalyst metal and, for example, aluminum is first melted and casted into ingots.

Typical alloy batches on a production scale amount to about ten to a couple hundred kg per ingot. According to DE 21 59 736 cooling times of up to two hours were obtained for this method. This corresponds to an average rate of cooling of about 0.2 K/s. In contrast to this, rates of $10^2$ to $10^6$ K/s and higher are achieved in processes where rapid cooling is applied (for example an atomizing process). The rate of cooling is affected in particular by the particle size and the cooling medium (see Materials Science and Technology edited by R. W. Chan, P. Haasen, E. J. Kramer, Vol. 15, Processing of Metals and Alloys, 1991, VCH-Verlag Weinheim, pages 57 to 110). A process of this type is used in EP 0 437 788 B 1 in order to prepare a Raney alloy powder. In that process the molten alloy at a temperature of 5 to 500° C. above its melting point is atomized and cooled using water and/or a gas.

To prepare a powder catalyst, the Raney alloy which can be made by a known process (i.e. according to EP 0 437 788 B1) is first finely milled, if it has not been produced in the desired powder form during preparation. Then the aluminum is partly (and if need be, totally) removed by extraction with alkalis such as, for example, caustic soda solution (other bases such as KOH are also suitable) to activate the alloy powder. These types of catalysts can be activated with most bases and acids to give varying results. Following extraction of the aluminum, the remaining catalytic power has a high specific surface area (BET), between 5 and 150 $m^2/g$, and is rich in active hydrogen. The activated catalyst powder is pyrophoric and stored under water or organic solvents or is embedded in organic compounds (e.g., distearylamine) which are solid at room temperature.

U.S. Pat. No. 6,423,872 describes the use of Ni catalysts that contain less than 5.5 wt % Al for the hydrogenation of nitrated aromatics. It describes the use of both commercially available standard activated Ni catalysts and supported Ni catalysts for the hydrogenation of nitrated aromatics, where problematic nickel aluminates are formed during this hydrogenation if their Al content is 5.5 wt % Al or higher.

These nickel aluminates can be in the form of takovite and/or takovite-like compounds and all of these nickel aluminates need to be removed from the desired amine before it is processed further. These nickel aluminates tend to form solids in the reactor and in the peripheral equipment (e.g., piping, settling tanks, filtration equipment, pumps and other equipment used in this process) that can deposit on their walls to decrease their heat transfer efficiency and to create blockages in the system.

Hence the formation of these nickel aluminates creates both safety hazards and a drop in productivity. The buildup of these nickel aluminates make it difficult to continue with the reaction and in such cases, one needs to shutdown the plant and clean out these deposits from the reactor and the peripheral equipment.

U.S. Pat. No. 6,423,872 also mentions the use of very specific alloy dopants limited to a definite list of elements that remain in the activated Ni catalyst after activation with caustic and the use of these resulting catalysts for the continuous hydrogenation of nitrated aromatics.

The conventional alloy doping elements from the groups IVA, VA, VIA and VIII of the periodic table of elements were specifically claimed in this patent. Additional Alloy doping elements such as titanium iron and chromium were also claimed.

U.S. Pat. No. 6,423,872 describes the use of a Ni catalyst having less than 5.5 wt % Al for the continuous hydrogenation of nitrated aromatics due to its lower formation of undesirable nickel aluminates during this hydrogenation. In principle, the less Al you have in the catalyst, the lower the amount of the nickel aluminates you will form. However these catalysts still form nickel aluminates and this technology does have its limits since the Al that is present in them is still considerably leachable under the conditions used for the hydrogenation of nitro-compounds such as nitrated aromatics.

U.S. Pat. No. 6,423,872 keeps the Al level lower than 5.5 wt % by changing the Al content of the alloy and/or increasing the intensity of the activation process. Increasing the Al content in the alloy will increase the amounts of Al-rich and more readily leachable phases such as $NiAl_3$ and the Al-eutectic phases. Another way to increase the amounts of these phases would be to perform the appropriate heat treatment to the alloy either after or during its production. Increasing the amounts of these readily leachable phases can also decrease the mechanical stability of these catalysts, thereby leading to a lower lifetime for the catalysts.

Hence lowering the Al content of the catalyst simply by increasing the amount of leachable phases in the precursor alloy does have its limitations.

Another method that U.S. Pat. No. 6,423,872 describes to decrease the Al content in the catalyst was to increase the intensity of the activation process by increasing the leaching temperature, pressure and other parameters that accelerate this process. However, not only does this increase the cost of the catalyst, but it also produces a sodium aluminate side product that is not salable and would need to be disposed of. Moreover if one is not careful during leaching, the newly formed sodium aluminate under these harsher conditions may deposit back on to the catalyst and block its catalytically active surface leading to lower activity and shorter catalyst life.

While the methods of U.S. Pat. No. 6,423,872 do decrease the level of leachable Al to some degree, they do not entirely solve the problems involved with the hydrogen of nitro-compounds, since most alloy activations used in catalyst production occur under different conditions than those of the continuous hydrogenation of nitro-compounds such as nitrated aromatic compounds. Thus the commercially applicable methods of U.S. Pat. No. 6,423,872 produce a catalyst that still has a considerable amount of Al in the catalyst that can be leached out during the hydrogenation of nitrated aromatic compounds.

Hence it is a goal of the present invention to produce a catalyst that generates lower levels of nickel aluminates buy minimizing the leachability of the remaining Al in the catalyst, regardless of the level of Al.

Surprisingly this problem is solved with activated Ni catalysts according to the invention.

The formation of takovite during the hydrogenation of nitro-compounds with an activated base metal catalyst can be greatly reduced, or even eliminated, by doping the catalyst with one or more elements from the list of Mg, Ca, Ba, Ti, Zr, Ce, Nb, Cr, Mo, W, Mn, Re, Fe, Co, Ir, Ni, Cu, Ag, Au, Bi, Rh and Ru by adsorption onto the surface of the catalyst during and/or after activation of the precursor alloy. The adsorption of one or more of the above mentioned elements after activation includes before, during and/or after washing the catalyst subsequent to activation. The adsorption of the doping element(s) can take place with existing compounds of the doping element(s) and/or with compounds of the doping element(s) that are formed in-situ during the doping process. The adsorption of the doping element(s) normally takes place in a liquid phase and the compounds of the doping elements can be soluble in the liquid medium or only slightly soluble in the liquid phase so that the rate of doping can be controlled by the solubility determined concentration of the doping element(s) in the slurry phase. One could also add inhibitors (e.g., chelating agents), accelerators (e.g., precipitating agents) and combinations thereof that control the rate of adsorption of the doping element(s) on to the catalytic surface. One could also use the gas phase to adsorb doping elements provided that care is taken to prevent the excessive oxidation and deactivation of the catalyst. In such cases, it could actually be possible to adsorb the promoting element(s) via techniques such as evaporation, sublimation and sputtering onto the catalytic surface. This use of adsorption methods for the doping of the catalyst is clearly different than the addition of the doping element(s) to the alloy prior to activation in that the adsorption method concentrates the doping element(s) onto the surface of the catalyst with very little, if any at all, of the doping element(s) being in the bulk of the catalyst particle. This surprisingly helps in inhibiting the formation of takovite. The preferred doping elements of the above mentioned list to be adsorbed onto the catalyst are Cr, Mo, Fe, Co, Ni, Cu, Ag and Au.

A further preferred embodiment of this invention is the addition of one or more of the doping elements from the list of Ti, Ce, V, Cr, Mo, W, Mn, Re, Fe, Ru, Co, Rh, Ir, Pd, Pt and Bi to the precursor alloy before activation followed by the adsorption of one or more doping elements from the list of Mg, Ca, Ba, Ti, Zr, Ce, V, Nb, Cr, Mo, W, Mn, Re, Fe, Ru, Co, Rh, Ir, Ni, Pd, Pt, Cu, Ag, Au and Bi during and/or after the activation of the alloy. In this preferred embodiment, the adsorbed doping element(s) may be added before, during and/or after washing the catalyst subsequent to its activation. The preferred elements for the doping in the alloy are one of more from the list of Ti, Ce, Cr, V, Mo, Fe, Ru, Pd, Pt and Co and the preferred elements for the subsequent doping via adsorption are Mg, Cr, V, Mo, Fe, Co, Ni, Cu, Ru, Pd, Pt, Ag and Au. The catalyst produced by introducing one or more of the above mentioned doping elements into the alloy followed by the adsorption of one or more of different and/or the same doping elements from the list mentioned above was found to be advantageous for the hydrogenation of nitro-compounds while greatly reducing, and in some cases eliminating, the formation of takovite.

The doping level of the preferred catalysts can range from 0.01 wt % to 10 wt % for each doping element and the Al content ranges from 0.05 wt % to 10 wt %.

Optimally the catalysts can contain between 0.01 and 1.9 wt.-% Fe.

Optimally the catalysts can contain between 0.01 and 2.4 wt.-% Cr.

Optimally the catalysts can contain between 0.01 and 1.9 wt.-% Fe and contain between 0.01 and 2.4 wt.-% Cr.

An especially useful catalyst for the hydrogenation of nitro-compounds without the formation of takovite was found to be a Ni/Al catalyst that was doped with Cu in combination with one or more elements from the list of Mg, Ti, Ce, V, Cr, Mo, W, Mn, Re, Fe, Ru, Co, Rh, Ir, Pd, Pt and Bi via their adsorption during and/or after the activation of the alloy. The preferred catalysts from this part of the present invention include the doping of the catalyst via adsorption with Cu together with one or more elements from the list of Mg, V, Cr, Mo, Fe, Ru, Co, Pd, Pt, Ag and Au. Another catalyst of this invention also includes doping the Ni/Al alloy with one or more elements from the list of Ti, Ce, V, Cr, Mo, W, Mn, Re, Fe, Ru, Co, Rh, Ir, Pd, Pt and Bi before activation followed by the adsorption of Cu onto the catalyst during and/or after the activation process. The catalyst of this invention can also be made by doping the Ni/Al alloy with one or more elements from the list of Ti, Ce, V, Cr, Mo, W, Mn, Re, Fe, Ru, Co, Rh, Ir, Pd, Pt and Bi before activation followed by the adsorption of Cu together with one or more doping from the list of Mg, Ti, Ce, V, Cr, Mo, W, Mn, Re, Fe, Ru, Co, Rh, Ir, Pd, Pt and Bi onto the catalyst during and/or after the activation process.

An especially useful catalyst for the hydrogenation of nitro-compounds without the formation of takovite was found to be a Ni/Al catalyst that was doped with Mo in combination with one or more elements from the list of Mg, Ti, Ce, V, Cr, Cu, W, Mn, Re, Fe, Ru, Co, Rh, Ir, Pd, Pt and Bi via their adsorption during and/or after the activation of the alloy. The preferred catalysts from this part of the present invention include the doping of the catalyst via adsorption with Mo together with one or more elements from the list of Mg, V, Cr, Cu, Fe, Ru, Co, Pd, Pt, Ag and Au. Another catalyst of this invention also includes doping the Ni/Al alloy with one or more elements from the list of Ti, Ce, V, Cr, Mo, W, Mn, Re, Fe, Ru, Co, Rh, Ir, Pd, Pt and Bi before activation followed by the adsorption of Mo onto the catalyst during and/or after the activation process. The catalyst of this invention can also be made by doping the Ni/Al alloy with one or more elements from the list of Ti, Ce, V, Cr, Mo, W, Mn, Re, Fe, Ru, Co, Rh, Ir, Pd, Pt and Bi before activation followed by the adsorption of Mo together with one or more doping from the list of Mg, Ti, Ce, V, Cr, Cu, W, Mn, Re, Fe, Ru, Co, Rh, Ir, Pd, Pt and Bi onto the catalyst during and/or after the activation process.

An especially useful catalyst for the hydrogenation of nitro-compounds without the formation of takovite was found to be a Ni/Al catalyst that was doped with Cr in combination with one or more elements from the list of Mg, Ti, Ce, V, Cr, Mo, W, Mn, Re, Fe, Ru, Co, Rh, Ir, Pd, Pt and Bi via their adsorption during and/or after the activation of the alloy. The preferred catalysts from this part of the present invention include the doping of the catalyst via adsorption with Cr together with one or more elements from the list of Mg, V, Cu, Mo, Fe, Ru, Co, Pd, Pt, Ag and Au. Another catalyst of this invention also includes doping the Ni/Al alloy with one or more elements from the list of Ti, Ce, V, Cr, Mo, W, Mn, Re, Fe, Ru, Co, Rh, Ir, Pd, Pt and Bi before activation followed by the adsorption of Cr onto the catalyst during and/or after the activation process. The catalyst of this invention can also be made by doping the Ni/Al alloy with one or more elements from the list of Ti, Ce, V, Cr, Mo, W, Mn, Re, Fe, Ru, Co, Rh, Ir, Pd, Pt and Bi before activation followed by the adsorption of Cr together with one or more doping from the list of Mg, Ti, Ce, V, Cu, Mo, W, Mn, Re, Fe, Ru, Co, Rh, Ir, Pd, Pt and Bi onto the catalyst during and/or after the activation process.

The powdered activated base metal catalysts (Raney-type catalysts) are typically used in either batch or continuous processes with stirred tank reactors. Batch processes are very flexible and under the right conditions, they are very economical for the hydrogenation of nitro-compounds to amines.

Another method involves the use of these powder catalysts in loop reactors where the reaction could occur in the vapor, trickle, aerosol or liquid phase. Loop, tube and stirred tank reactors can be used continuously for this process, where the nitro-compound is fed into the reactor at a rate in which it is immediately hydrogenated to completion or in some cases almost to completion when a second hydrogenation reactor (or even more) is used to hydrogenate the remaining amounts of the nitro-compound and its possible intermediates. During the continuous hydrogenation process, the same amount of the desired amine is removed from of the reaction system at the same rate as the nitro-compound is added to maintain the overall volume of the reaction medium in the reactor. In the case of loop and tube reactors, this reaction may be done in a circulation mode where the nitro-compound is introduced in one part of the circulating reaction stream and the finished product mixture is taken out of another part.

This reaction can take place in the presence of one or more solvents (for example but not limited to alcohols such as methanol and ethanol) or it can take place in the product mixture of the resulting amine and water. The advantages of using the product mixture for the reaction medium is that one does not need to buy the solvent and it does not need to be removed from the reaction mixture or possibly purified before being used again. Another option would be to perform the reaction in only the desired amine and to use a high enough reaction temperature so that the water is immediately distilled away from the reaction slurry and so that the desired amine remains in a liquid form. This is especially important for amines such as toluenediamine, where it needs to be kept in the molten state if it is to be used as the reaction medium without the assistance of solvents that maintain the liquid properties of the reaction slurry.

In general, the powder catalysts of this invention can be used in any reaction system and in any reaction process that is suitable for the hydrogenation of nitro-compounds to amines that utilize powder catalysts.

This invention includes the process for the hydrogenation of nitro-compounds with an activated Ni catalyst which is characterized in that is doped with one or more elements from the list of Mg, Ca, Ba, Ti, Zr, Ce, Nb, Cr, Mo, W, Mn, Re, Fe, Co, Ir, Ni, Cu, Ag, Au, Bi, Rh and Ru by adsorption onto the surface of the catalyst during and/or after activation of the precursor alloy as described previously. The preferred doping elements of the above mentioned list to be adsorbed onto the catalyst are Cr, Mo, Fe, Co, Ni, Cu, Ag and Au. The doping level of the preferred catalyst can range from 0.01 wt % to 10 wt % for each doping element and the Al content ranges from 0.05 wt % to 10 wt %.

A further embodiment of this invention is the process for the hydrogenation of nitro-compounds with an activated Ni catalyst which is doped with one or more elements from the list of Ti, Ce, V, Cr, Mo, W, Mn, Re, Fe, Ru, Co, Rh, Ir, Pd, Pt and Bi to the precursor alloy before activation followed by the adsorption of one or more doping elements from the list of Mg, Ca, Ba, Ti, Zr, Ce, V, Nb, Cr, Mo, W, Mn, Re, Fe, Ru, Co, Rh, Ir, Ni, Pd, Pt, Cu, Ag, Au and Bi during and/or after the activation of the alloy. In this preferred embodiment, the adsorbed doping element(s) may be added before, during and/or after washing the catalyst subsequent to its activation. The preferred elements for the doping in the alloy are one of more from the list of Ti, Ce, Cr, V, Mo, Fe, Ru, Pd, Pt and Co and the preferred elements for the subsequent doping via adsorption are Mg, Cr, V, Mo, Fe, Co, Ni, Cu, Ru, Pd, Pt, Ag and Au. The doping level of the preferred catalyst can range from 0.01 wt % to 10 wt % for each doping element and the Al content ranges from 0.05 wt % to 10 wt %.

This invention includes the process for the hydrogenation of nitrated aromatics with an activated Ni catalyst which is characterized in that is doped with one or more elements from the list of Mg, Ca, Ba, Ti, Zr, Ce, Nb, Cr, Mo, W, Mn, Re, Fe, Co, Ir, Ni, Cu, Ag, Au, Bi, Rh and Ru by adsorption onto the surface of the catalyst during and/or after activation of the precursor alloy as described previously. The preferred doping elements of the above mentioned list to be adsorbed onto the catalyst are Cr, Mo, Fe, Co, Ni, Cu, Ag and Au. The doping level of the preferred catalyst can range from 0.01 wt % to 10 wt % for each doping element and the Al content ranges from 0.05 wt % to 10 wt %.

A further embodiment of this invention is the process for the hydrogenation of nitrated aromatics with an activated Ni catalyst which is doped with one or more elements from the list of Ti, Ce, V, Cr, Mo, W, Mn, Re, Fe, Ru, Co, Rh, Ir, Pd, Pt and Bi to the precursor alloy before activation followed by the adsorption of one or more doping elements from the list of Mg, Ca, Ba, Ti, Zr, Ce, V, Nb, Cr, Mo, W, Mn, Re, Fe, Ru, Co, Rh, Ir, Ni, Pd, Pt, Cu, Ag, Au and Bi during and/or after the activation of the alloy. In this preferred embodiment, the adsorbed doping element(s) may be added before, during and/or after washing the catalyst subsequent to its activation. The preferred elements for the doping in the alloy are one of more from the list of Ti, Ce, Cr, V, Mo, Fe, Ru, Pd, Pt and Co and the preferred elements for the subsequent doping via adsorption are Mg, Cr, V, Mo, Fe, Co, Ni, Cu, Ru, Pd, Pt, Ag and Au. The doping level of the preferred catalyst can range from 0.01 wt % to 10 wt % for each doping element and the Al content ranges from 0.05 wt % to 10 wt %.

This invention includes the process for the continuous hydrogenation of nitrated aromatics with an activated Ni catalyst which is characterized in that is doped with one or more elements from the list of Mg, Ca, Ba, Ti, Zr, Ce, Nb, Cr, Mo, W, Mn, Re, Fe, Co, Ir, Ni, Cu, Ag, Au, Bi, Rh and Ru by adsorption onto the surface of the catalyst during and/or after activation of the precursor alloy as described previously. The preferred doping elements of the above mentioned list to be adsorbed onto the catalyst are Cr, Mo, Fe, Co, Ni, Cu, Ag and Au. The doping level of the preferred catalyst can range from 0.01 wt % to 10 wt % for each doping element and the Al content ranges from 0.05 wt % to 10 wt %.

A further embodiment of this invention is the continuous process for the hydrogenation of nitrated aromatics with an activated Ni catalyst which is doped with one or more elements from the list of Ti, Ce, V, Cr, Mo, W, Mn, Re, Fe, Ru, Co, Rh, Ir, Pd, Pt and Bi to the precursor alloy before activation followed by the adsorption of one or more doping elements from the list of Mg, Ca, Ba, Ti, Zr, Ce, V, Nb, Cr, Mo, W, Mn, Re, Fe, Ru, Co, Rh, Ir, Ni, Pd, Pt, Cu, Ag, Au and Bi during and/or after the activation of the alloy. In this preferred embodiment, the adsorbed doping element(s) may be added before, during and/or after washing the catalyst subsequent to its activation. The preferred elements for the doping in the alloy are one of more from the list of Ti, Ce, Cr, V, Mo, Fe, Ru, Pd, Pt and Co and the preferred elements for the subsequent doping via adsorption are Mg, Cr, V, Mo, Fe, Co, Ni, Cu, Ru, Pd, Pt, Ag and Au. The doping level of the preferred catalyst can range from 0.01 wt % to 10 wt % for each doping element and the Al content ranges from 0.05 wt % to 10 wt %.

There are many types of nitro-compound hydrogenations performed in industry. One of the more commercially interesting and technically challenging is the hydrogenation of dinitrotoluene (DNT) to toluenediamine (TDA). This hydrogenation is performed with activated Ni catalysts at temperatures ranging from room temperature to 210° C. and pressures ranging from atmospheric pressure to 200 bar. The preferred reaction conditions are within the ranges of 50° to 180° C. and 3 to 80 bar. This reaction can be performed in an excess of hydrogen or under a stoichiometric amount of hydrogen.

In U.S. Pat. No. 6,423,872, the reaction conditions for the continuous hydrogenation of DNT were 20 bar hydrogen at 150° C. with 0.7 grams of activated Ni catalyst and a DNT feed that kept the level of DNT below 1000 ppm during this hydrogenation. In U.S. Pat. No. 3,935,264, the hydrogenation of DNT was performed with methanol as a solvent under the pressure of 28.5 bar hydrogen and 120° C. over the activated Ni catalyst.

Recently in U.S. Pat. No. 6,005,143, it was found that one could achieve satisfactory results for the hydrogenation of DNT to TDA over a Ni/Pd catalyst supported on a monolith in the presence of methanol with 16 bar hydrogen and temperatures ranging from 135 to 155° C.

Typically fixed bed hydrogenation processes require higher hydrogen pressures than their slurry phase counterparts, indicating that pressures of ~16 Bar should also be suitable for the reactions performed here. U.S. Pat. No. 4,224,249 also showed this to be true as a Raney-type Ni catalyst was successfully used at 130° C. and 160 psig (12 bar) for the hydrogenation of dinitrotoluene (DNT) in both the batch and the incremental feed modes of operation. The incremental feed mode of operation was used to simulate the conditions in which DNT is continuously hydrogenated on a industrial scale.

The hydrogenation of nitro-compounds can take place in the vapor, slurry, trickle, aerosol and/or liquid phase. The reaction could be performed as a batch process or it could be performed as a continuous process. The continuous processes may involve, but they are not limited to, a type of circulation process. This invention also includes a continuous process where the nitro-compound is added at a rate that is the same or slower than the rate of hydrogenation, so that the concentration of the nitro-compound is kept to a very low level. The feeding rate of the nitro-compound may be so low that the level of the nitro-compound is 1000 ppm or lower. This invention also includes the use of the previously mentioned catalyst of this invention in a continuous process that utilizes a second hydrogenation reactor (or more) to hydrogenate any nitro-compounds and/or intermediates that are remaining from the hydrogenation in the first hydrogenation reactor.

The nitro-compound hydrogenation of this invention may take place in the presence of the neat nitro-compound, at high concentrations of the reactant, at very low concentrations of the reactant and/or in the presence of the product mixture that would be acting like a solvent. This hydrogenation may also take place in the presence of practically only the desired amine if the water is removed in a satisfactory method (e.g., distillation) during the reaction. The nitro-compound hydrogenation of this invention may take place in the presence of a solvent. The reactor type could be, but is not limited to, a stirred tank reactor, a continuous stirred tank reactor, a loop reactor or a tube reactor. This nitro-compound hydrogenation may occur between atmospheric pressure and 200 bars of hydrogen and the temperature can range from ~10° C. to 210° C.

This invention encompasses the hydrogenation of nitrated aromatics and this may occur either as a batch or a continuous process over the above mentioned catalysts. This invention also includes the hydrogenation of DNT to TDA as either a batch process or a continuous process with the above described catalysts.

This invention also includes the catalysts having the following properties:

An activated Ni/Al catalyst that was doped with Cu via adsorption onto the surface of the catalyst during and/or after activation in combination with one or more elements from the list of Mg, Ti, Ce, V, Cr, Mo, W, Mn, Re, Fe, Ru, Co, Rh, Ir, Pd, Pt, Bi, Ag and Au via their adsorption during and/or after the activation of the alloy. The preferred catalysts from this part of the present invention include the doping of the catalyst via adsorption with Cu together with one or more elements from the list of Mg, V, Cr, Mo, Fe, Co, Pd, Pt and Au. Another catalyst of this invention also includes doping the Ni/Al alloy with one or more elements from the list of Mg, Ti, Ce, V, Cr, Mo, W, Mn, Re, Fe, Ru, Co, Rh, Ir, Pd, Pt and Bi before activation followed by the adsorption of Cu onto the catalyst during and/or after the activation process. The catalyst of this invention can also be made by doping the Ni/Al alloy with one or more elements from the list of Mg, Ti, Ce, V, Cr, Mo, W, Mn, Re, Fe, Ru, Co, Rh, Ir, Pd, Pt and Bi before activation followed by the adsorption of Cu together with one or more doping from the list of Mg, Ti, Ce, V, Cr, Mo, W, Mn, Re, Fe, Ru, Co, Rh, Ir, Pd, Pt, Bi, Ag and Au onto the catalyst during and/or after the activation process.

An activated Ni/Al catalyst that was doped with Mo in combination with one or more elements from the list of Mg, Ti, Ce, V, Cr, Cu, W, Mn, Re, Fe, Ru, Co, Rh, Ir, Pd, Pt, Bi, Ag and Au via their adsorption during and/or after the activation of the alloy. The preferred catalysts from this part of the present invention include the doping of the catalyst via adsorption with Mo together with one or more elements from the list of Mg, V, Cr, Cu, Fe, Pd, Pt and Au. Another catalyst of this invention also includes doping the Ni/Al alloy with one or more elements from the list of Mg, Ti, Ce, V, Cr, Mo, W, Mn, Re, Fe, Ru, Co, Rh, Ir, Pd, Pt and Bi before activation followed by the adsorption of Mo onto the catalyst during and/or after the activation process. The catalyst of this invention can also be made by doping the Ni/Al alloy with one or more elements from the list of Mg, Ti, Ce, V, Cr, Mo, W, Mn, Re, Fe, Ru, Co, Rh, Ir, Pd, Pt and Bi before activation followed by the adsorption of Mo together with one or more doping from the list of Mg, Ti, Ce, V, Cr, Cu, W, Mn, Re, Fe, Ru, Co, Rh, Ir, Pd, Pt, Bi, Ag and Au onto the catalyst during and/or after the activation process.

An activated Ni/Al catalyst that was doped with Cr in combination with one or more elements from the list of Mg, Ti, Ce, V, Cu, Mo, W, Mn, Re, Fe, Ru, Co, Rh, Ir, Pd, Pt, Bi, Ag and Au via their adsorption during and/or after the activation of the alloy. The preferred catalysts from this part of the present invention include the doping of the catalyst via adsorption with Cr together with one or more elements from the list of Mg, V, Cu, Mo, Fe, Co, Pd, Pt and Au. Another catalyst of this invention also includes doping the Ni/Al alloy with one or more elements from the list of Mg, Ti, Ce, V, Cr, Mo, W, Mn, Re, Fe, Ru, Co, Rh, Ir, Pd, Pt and Bi before activation followed by the adsorption of Cr onto the catalyst during and/or after the activation process. The catalyst of this invention can also be made by doping the Ni/Al alloy with one or more elements from the list of Mg, Ti, Ce, V, Cr, Mo, W, Mn, Re, Fe, Ru, Co, Rh, Ir, Pd, Pt and Bi before activation followed by the adsorption of Cr together with one or more doping from the list of Mg, Ti, Ce, V, Cu, Mo, W, Mn, Re, Fe, Ru, Co, Rh, Ir, Pd, Pt, Bi, Ag and Au onto the catalyst during and/or after the activation process.

APPLICATION EXAMPLE 1

Figure 1:
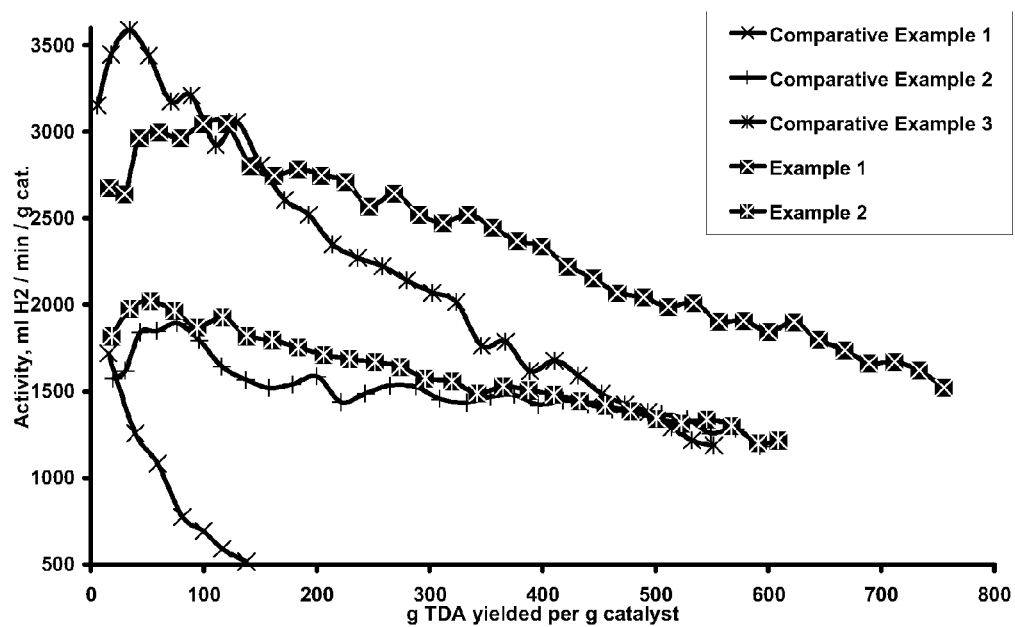
FIG. 1 is a graph showing DNT pulse hydgenation data for CE1, CE2, CE3, E1 and E2.
Figure 2:
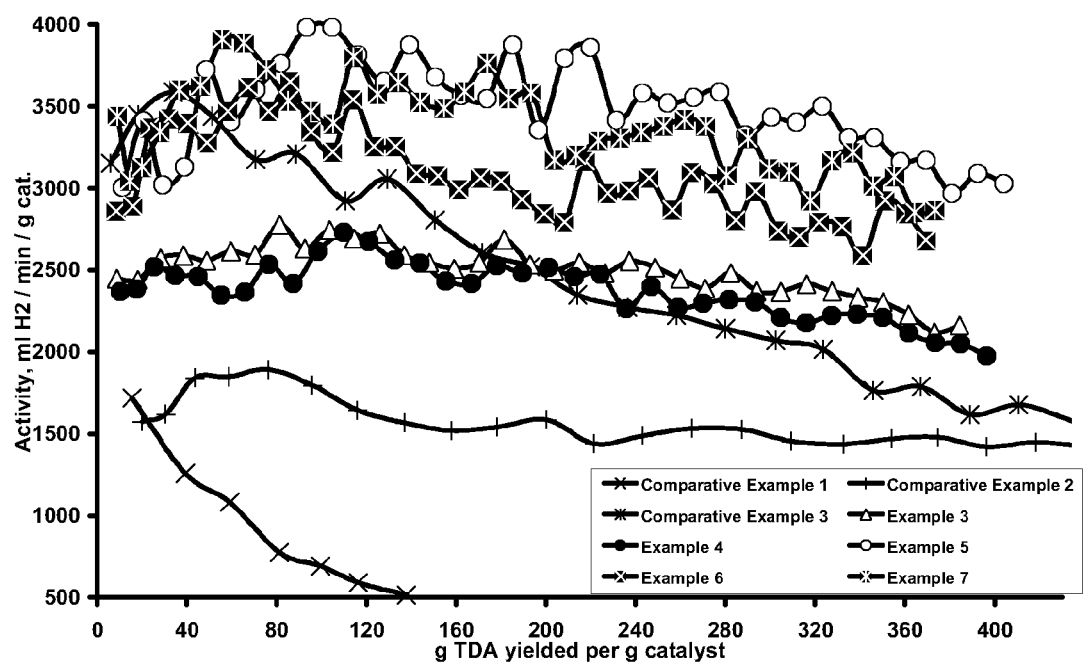
FIG. 2 is a graph showing DNT pulse hydrogenation data for CE1, CE2, CE3, E3, E4, E5, E6 and E7.

The pulse hydrogenation of dinitrotoluene (DNT) to toluenediamine (TDA).

DNT is typically hydrogenated in an industrial setting via a continuous mode, where the DNT feed rate is slow enough to keep its concentration low enough so that it doesn't poison the catalyst or become a safety hazard. This means that the hydrogenation rate will be dependent of the DNT feed rate. The goal of our pulse hydrogenation method was to keep the DNT concentration low enough so that it would be comparable to the industrial setting while measuring the activity of the catalyst. We were able to do so by pulsing in the DNT feed at a rate that was slightly faster than the rate of hydrogenation so that we could measure catalyst activity while keeping the time of the slight excess of DNT to a minimum. It was also decided to use the reaction pressure and temperature conditions similar to those described in U.S. Pat. No. 4,224,249, U.S. Pat. No. 6,423,872 and U.S. Pat. No. 6,005,143.

The pulse hydrogenation method was started by placing 150 or 300 milligrams of catalyst, 101 grams of TDA and 59 grams of water (the reaction's stoichiometric TDA-to-water ratio) into a 500 ml autoclave. The autoclave was then closed, purged with nitrogen 3 times, purged with hydrogen 3 times and heated to the reaction temperature of 140° C. over a period of 20 minutes while the reactor was stirring at 300 rpm and kept under 5 bar hydrogen. Once the autoclave reached 140° C., the hydrogen pressure was adjusted to 15 bar hydrogen and the stirring rate was increased to 1700 rpm. The reaction was then started by pulsing 4 milliliters of molten DNT into the reactor over 30 seconds with an HPLC pump. The HPLC pump head, the DNT reservoir and all the stainless tubing used for the transport of DNT was kept at 95° C. to keep the DNT molten. A Büchi hydrogen press flow controller (bpc 9901) was used to monitor the hydrogen consumption and once the reaction stopped to consume hydrogen, another pulse of DNT was introduced at the same feed rate. This procedure was continued until a maximum of 45 pulses had been introduced. The data from these hydrogenations can be seen in graph 1, graph 2 and in data tables 3 to 13.

APPLICATION EXAMPLE 2

The batch hydrogenation of nitrobenzene to aniline.

The low pressure hydrogenation of nitrobenzene was carried out over 1.5 grams of catalyst in 110 ml of a 9.1 wt % nitrobenzene ethanolic solution at 25° C. and atmospheric pressure. A baffled glass reactor outfitted with a bubbling stirrer spinning at 2000 rpm was used for these hydrogenations. The results of these hydrogenations are listed in table 1.

TABLE 1

The batch nitrobenzene hydrogenation data.

| Catalyst | Nitrobenzene Activity ml $H_2$/min/gram catalyst |
|---|---|
| Comparative Example 1 | 61 |
| Comparative Example 2 | 49 |
| Example 7 | 80 |

APPLICATION EXAMPLE 3

The determination of the catalyst's ability to form nickel aluminates (e.g., takovite).

U.S. Pat. No. 6,423,872 describes a method for the determination of the catalyst's ability to form nickel aluminates (e.g., takovite). This method involved putting the catalyst together with TDA at the temperature of 150° C. for 1 month. The tube was then opened and the catalyst was examined by X-Ray diffraction. It was found that the compound built up on the catalyst was takovite and its structure was shown by X-Ray diffraction to be the same as that of the deposits observed on the walls of an industrial DNT hydrogenation reactor and its peripheral equipment.

We performed a similar test for our studies here.

To determine the catalyst's ability to form takovite, 0.2 grams of the catalyst was placed together with 3.5 grams of a 63 wt % TDA and 37 wt % water mixture in a sealed tube for 3 weeks at 150° C. After the 3 weeks, the catalyst was removed and its takovite residues were analyzed by X-Ray diffraction. The takovite peak heights were then measured at the 12, 24, 35, 40 and 47 °2 theta positions. The nickel peak height at the 52 °2 theta position was also measured and it was the ratios of the individual takovite peak heights to the nickel peak height that was used to compare the different catalysts to each other. The relative ratios for these °2 theta positions were consistent enough for the different catalysts so that it was possible to consider using the ratio of the sum of the takovite peak heights for the 12, 24, 35, 40 and 47 °2 Theta positions to the nickel peak height at 52 °2 theta for this determination.

The data from these experiments are shown in table 2 and the catalysts with the higher takovite formation had the higher takovite-to-Ni peak height ratios. By comparing the catalysts of the same Al content to each other, one can see that the embodiments of this patent lead to lower levels of takovite formation. Only comparative example 1 (CE1) formed a hard version of takovite and the others examples described here only formed soft takovite, if they formed takovite at all.

TABLE 2

The x-ray diffraction data for the takovite deposits on the used activated nickel catalysts.

| Example number | Takovite peak heights (mm) at the below listed °2 ⊖ positions | | | | | Ni at 52 °2⊖ | Ratio of takovite peak heights to the Ni peak peak height | | | | | |
|---|---|---|---|---|---|---|---|---|---|---|---|---|
| | 12 | 24 | 35 | 40 | 47 | | 12 | 24 | 35 | 40 | 47 | Sum |
| CE1 | 47 | 33 | 22 | 26 | 22.5 | 3.0 | 15.7 | 11 | 7.3 | 8.7 | 7.5 | 50.2 |
| CE2 | 19.5 | 12.0 | 12.0 | 8.0 | 7.0 | 12.5 | 1.6 | 1.0 | 1.0 | 0.6 | 0.6 | 4.7 |

TABLE 2-continued

The x-ray diffraction data for the takovite deposits on the used activated nickel catalysts.

| Example number | Takovite peak heights (mm) at the below listed °2Θ positions | | | | | Ni at 52 °2Θ | Ratio of takovite peak heights to the Ni peak peak height | | | | | |
|---|---|---|---|---|---|---|---|---|---|---|---|---|
| | 12 | 24 | 35 | 40 | 47 | | 12 | 24 | 35 | 40 | 47 | Sum |
| CE3 | 54 | 31.5 | 25.5 | 18.5 | 17 | 7.0 | 7.7 | 4.5 | 3.6 | 2.6 | 2.4 | 20.9 |
| E1 | 12 | 8.0 | 8.0 | 6.0 | 5.0 | 15 | 0.8 | 0.5 | 0.5 | 0.4 | 0.3 | 2.6 |
| E2 | 0.0 | 0.0 | 0.0 | 0.0 | 0.0 | 16.0 | 0.0 | 0.0 | 0.0 | 0.0 | 0.0 | 0.0 |
| E3 | 12 | 8.0 | 8.0 | 5.0 | 4.5 | 15 | 0.8 | 0.5 | 0.5 | 0.3 | 0.3 | 2.5 |
| E4 | 0.0 | 0.0 | 0.0 | 0.0 | 0.0 | 14 | 0.0 | 0.0 | 0.0 | 0.0 | 0.0 | 0.0 |
| E5 | 23 | 12.5 | 12.0 | 8.0 | 7.0 | 12.5 | 1.8 | 1.0 | 1.0 | 0.6 | 0.6 | 5.0 |
| E6 | 18.5 | 10.5 | 11.0 | 7.0 | 6.0 | 12.5 | 1.5 | 0.8 | 0.9 | 0.6 | 0.5 | 4.2 |
| E8 | 0.0 | 0.0 | 0.0 | 0.0 | 0.0 | 13 | 0.0 | 0.0 | 0.0 | 0.0 | 0.0 | 0.0 |

COMPARATIVE EXAMPLE 1

An alloy containing Ni, Al, Cr and Fe was activated in an aqueous 20 wt.-% NaOH suspension between 100 and 110° C. resulting in activated Ni catalyst containing 8.8 wt % Al, 2.5 wt % Cr and 2 wt % Fe with an average particle size value of 35 μm was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 50.2. The individual takovite-to-nickel ratios of the x-ray peaks at 12, 24, 35, 40 and 47 °2 theta can be seen in table 2. This catalyst was used for the batch hydrogenation of nitrobenzene to aniline as described in application example 2. The nitrobenzene hydrogenation activity of this catalyst was found to be 61 ml $H_2$/min/gram of catalyst and additional information can be seen in table 1. As described in application example 1, 150 milligrams of this catalyst were used for the pulse hydrogenation of dinitrotolunene to toluenediamine. The selectivity of this reaction was greater than 90% toluenediamine and the activity data points are given below in table 3 and graph 1.

TABLE 3

The dinitrotoluene hydrogenation data for comparative example 1.

| grams TDA yielded per gram of catalyst | Hydrogenation Activity ml $H_2$ per minute per gram of catalyst |
|---|---|
| 15.5 | 1719 |
| 39.4 | 1258 |
| 59.1 | 1082 |
| 81.2 | 775 |
| 99.7 | 692 |
| 116.4 | 591 |
| 137.9 | 515 |

COMPARATIVE EXAMPLE 2

An alloy containing Ni, Al and Fe was activated in an aqueous 20 wt.-% NaOH suspension between 100 and 110° C. resulting in an activated Ni catalyst containing 4 wt % Al, and 0.2 wt % Fe with an average particle size value of 28 μm was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 4.7. The individual takovite-to-nickel ratios of the x-ray peaks at 12, 24, 35, 40 and 47 °2 theta can be seen in table 2. This catalyst was used for the batch hydrogenation of nitrobenzene to aniline as described in application example 2. The nitrobenzene hydrogenation activity of this catalyst was found to be 49 ml $H_2$/min/gram of catalyst and additional information can be seen in table 1. As described in application example 1, 150 milligrams of this catalyst were used for the pulse hydrogenation of dinitrotoluene to toluenediamine. The selectivity of this reaction was greater than 99% toluenediamine and the activity data points are given below in table 4 and graph 1.

TABLE 4

The dinitrotoluene hydrogenation data for comparative example 2.

| grams TDA yielded per gram of catalyst | Hydrogenation Activity ml $H_2$ per minute per gram of catalyst |
|---|---|
| 20 | 1575 |
| 31 | 1620 |
| 44 | 1842 |
| 59 | 1848 |
| 77 | 1893 |
| 96 | 1796 |
| 116 | 1644 |
| 137 | 1567 |
| 158 | 1520 |
| 179 | 1541 |
| 200 | 1586 |
| 222 | 1439 |
| 243 | 1488 |
| 265 | 1533 |
| 288 | 1527 |
| 309 | 1456 |
| 333 | 1436 |
| 354 | 1469 |
| 375 | 1480 |
| 397 | 1422 |
| 418 | 1447 |
| 440 | 1424 |
| 462 | 1393 |
| 484 | 1385 |
| 506 | 1370 |
| 528 | 1341 |
| 549 | 1259 |
| 571 | 1283 |
| 593 | 1183 |

COMPARATIVE EXAMPLE 3

An alloy containing Ni, Al, Cr and Fe was activated in an aqueous 20 wt.-% NaOH suspension between 100 and 110° C. resulting in an activated Ni catalyst containing 6.3 wt % Al, 1.9 wt % Cr and 0.8 wt % Fe with an APS value of 29 μm was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 20.9. The individual takovite-to-nickel ratios of the x-ray peaks at 12, 24, 35, 40 and 47 °2 theta can be seen in table 2. As described in application example 1, 150 milligrams of this catalyst were used for the pulse hydrogenation of dinitrotoluene to toluenediamine. The selectivity of this reaction was greater than 99% toluenediamine and the activity data points are given below in table 5 and graph 1.

TABLE 5

The dinitrotoluene hydrogenation data for comparative example 3.

| grams TDA yielded per gram of catalyst | Hydrogenation Activity ml $H_2$ per minute per gram of catalyst |
|---|---|
| 6 | 3154 |
| 18 | 3447 |
| 34 | 3587 |
| 51 | 3440 |
| 71 | 3175 |
| 89 | 3210 |
| 111 | 2924 |
| 129 | 3057 |
| 151 | 2808 |
| 172 | 2607 |
| 193 | 2521 |
| 214 | 2350 |
| 237 | 2273 |
| 258 | 2223 |
| 280 | 2142 |
| 302 | 2070 |
| 324 | 2016 |
| 346 | 1764 |
| 367 | 1788 |
| 389 | 1618 |
| 411 | 1677 |
| 432 | 1591 |
| 453 | 1486 |
| 473 | 1424 |
| 494 | 1380 |
| 514 | 1292 |
| 532 | 1216 |
| 552 | 1187 |

EXAMPLE 1

An alloy containing Ni, Al and Fe was activated in an aqueous 20 wt.-% NaOH suspension between 100 and 110° C. resulting in an activated Ni catalyst containing 3.43 wt % Al and 0.2 wt % Fe that was doped with an aqueous solution of $CrO_3$ to the final Cr content of 0.5 wt % Cr. This catalyst had an APS value of 29 μm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 2.6. The individual takovite-to-nickel ratios of the x-ray peaks at 12, 24, 35, 40 and 47 °2 theta can be seen in table 2. As described in application example 1, 150 milligrams of this catalyst were used for the pulse hydrogenation of dinitrotoluene to toluenediamine. The selectivity of this reaction was greater than 99.5% toluenediamine and the activity data points are given below in table 6 and graph 1. Although the initial activity of this catalyst was lower than that of CE3, this catalyst had a far lower rate of deactivation than the CE3 and it became more active than CE3 during the reaction and remained more active. As the reaction proceeded, the deactivation rate of the catalyst became very close to zero. Hence, this catalyst is considerably better than CE3.

TABLE 6

The dinitrotoluene hydrogenation data for example 1.

| grams TDA yielded per gram of catalyst | Hydrogenation Activity ml $H_2$ per minute per gram of catalyst |
|---|---|
| 16 | 2678 |
| 30 | 2641 |
| 43 | 2965 |
| 61 | 2999 |
| 80 | 2965 |
| 100 | 3048 |
| 120 | 3049 |
| 141 | 2802 |
| 163 | 2747 |
| 184 | 2785 |
| 204 | 2749 |
| 226 | 2713 |
| 247 | 2570 |
| 269 | 2644 |
| 291 | 2521 |
| 312 | 2476 |
| 334 | 2521 |
| 356 | 2449 |
| 378 | 2369 |
| 400 | 2338 |
| 423 | 2223 |
| 445 | 2154 |
| 467 | 2070 |
| 490 | 2044 |
| 511 | 1989 |
| 534 | 2011 |
| 556 | 1907 |
| 578 | 1910 |
| 600 | 1844 |
| 623 | 1900 |
| 645 | 1799 |
| 668 | 1739 |
| 689 | 1664 |
| 712 | 1672 |
| 734 | 1622 |
| 755 | 1521 |

EXAMPLE 2

An alloy containing Ni, Al and Fe was activated in an aqueous 20 wt.-% NaOH suspension between 100 and 110° C. resulting in an activated Ni catalyst containing 3.46 wt % Al and 0.2 wt % Fe that was doped with an aqueous solution of $CuSO_4$ to the final Cu content of 0.1 wt % Cu. This catalyst had an APS value of 29 μm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 0.0. The individual takovite-to-nickel ratios of the x-ray peaks at 12, 24, 35, 40 and 47 °2 theta can be seen in table 2. As described in application example 1, 150 milligrams of this catalyst were used for the pulse hydrogenation of dinitrotoluene to toluenediamine. The selectivity of this reaction was greater than 99.5% toluenediamine and the activity data points are given below in table 7 and graph 1. Although the initial activity of this catalyst was lower than that of CE3, this catalyst had a far lower rate of deactivation than the CE3 and it became more active than CE3 during the reaction and remained more active. As the reaction proceeded, the deactivation rate of the catalyst became very close to zero. Hence, this catalyst is considerably better than CE3. Unlike CE3, this catalyst does not form takovite and this will lead to further improvements in the use of this catalyst for the hydrogenation of nitro-compounds.

TABLE 7

The dinitrotoluene hydrogenation data for example 2.

| grams TDA yielded per gram of catalyst | Hydrogenation Activity ml H$_2$ per minute per gram of catalyst |
|---|---|
| 19 | 1821 |
| 34 | 1980 |
| 53 | 2021 |
| 74 | 1966 |
| 94 | 1871 |
| 117 | 1928 |
| 139 | 1821 |
| 161 | 1797 |
| 184 | 1754 |
| 206 | 1714 |
| 229 | 1688 |
| 252 | 1671 |
| 274 | 1643 |
| 296 | 1576 |
| 320 | 1558 |
| 342 | 1489 |
| 365 | 1527 |
| 388 | 1507 |
| 410 | 1481 |
| 433 | 1447 |
| 456 | 1419 |
| 478 | 1385 |
| 501 | 1344 |
| 523 | 1316 |
| 546 | 1340 |
| 567 | 1303 |
| 591 | 1202 |
| 609 | 1218 |

EXAMPLE 3

An alloy containing Ni, Al and Fe was activated in an aqueous 20 wt.-% NaOH suspension between 100 and 110° C. resulting in an activated Ni catalyst containing 3.87 wt % Al and 0.22 wt % Fe that was doped with an aqueous solution of an ammonium molybdate salt to the final Mo content of 0.11 wt % Mo. This catalyst had an APS value of 17 μm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 2.5. The individual takovite-to-nickel ratios of the x-ray peaks at 12, 24, 35, 40 and 47 °2 theta can be seen in table 2. As described in application example 1, 300 milligrams of this catalyst were used for the pulse hydrogenation of dinitrotoluene to toluenediamine. The selectivity of this reaction was greater than 99.5% toluenediamine and the activity data points are given below in table 8 and graph 2

TABLE 8

The dinitrotoluene hydrogenation data for example 3.

| grams TDA yielded per gram of catalyst | Hydrogenation Activity ml H$_2$ per minute per gram of catalyst |
|---|---|
| 9 | 2449 |
| 18 | 2441 |
| 28 | 2572 |
| 39 | 2590 |
| 49 | 2560 |

TABLE 8-continued

The dinitrotoluene hydrogenation data for example 3.

| grams TDA yielded per gram of catalyst | Hydrogenation Activity ml H$_2$ per minute per gram of catalyst |
|---|---|
| 60 | 2617 |
| 71 | 2597 |
| 81 | 2778 |
| 93 | 2633 |
| 104 | 2747 |
| 115 | 2694 |
| 126 | 2725 |
| 137 | 2594 |
| 148 | 2546 |
| 159 | 2510 |
| 170 | 2546 |
| 181 | 2688 |
| 193 | 2535 |
| 204 | 2500 |
| 215 | 2546 |
| 226 | 2483 |
| 237 | 2556 |
| 249 | 2518 |
| 260 | 2449 |
| 271 | 2389 |
| 283 | 2483 |
| 294 | 2372 |
| 305 | 2368 |
| 316 | 2416 |
| 328 | 2372 |
| 339 | 2334 |
| 350 | 2305 |
| 362 | 2228 |
| 373 | 2119 |
| 384 | 2161 |
| 396 | 2117 |

EXAMPLE 4

An alloy containing Ni, Al and Fe was activated in an aqueous 20 wt.-% NaOH suspension between 100 and 110° C. resulting in an activated Ni catalyst containing 3.81 wt % Al and 0.21 wt % Fe that was doped with an aqueous solution of CuSO$_4$ to the final Cu content of 0.09 wt % Cu. This catalyst had an APS value of 20 μm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 0.0. The individual takovite-to-nickel ratios of the x-ray peaks at 12, 24, 35, 40 and 47 °2 theta can be seen in table 2. As described in application example 1, 300 milligrams of this catalyst were used for the pulse hydrogenation of dinitrotoluene to toluenediamine. The selectivity of this reaction was greater than 99.5% toluenediamine and the activity data points are given below in table 9 and graph 2

TABLE 9

The dinitrotoluene hydrogenation data for example 4.

| grams TDA yielded per gram of catalyst | Hydrogenation Activity ml H$_2$ per minute per gram of catalyst |
|---|---|
| 10 | 2369 |
| 18 | 2384 |
| 25 | 2521 |
| 35 | 2467 |
| 45 | 2460 |
| 55 | 2348 |
| 66 | 2365 |

TABLE 9-continued

The dinitrotoluene hydrogenation data for example 4.

| grams TDA yielded per gram of catalyst | Hydrogenation Activity ml H$_2$ per minute per gram of catalyst |
|---|---|
| 76 | 2536 |
| 87 | 2419 |
| 98 | 2614 |
| 110 | 2730 |
| 121 | 2676 |
| 133 | 2560 |
| 144 | 2544 |
| 155 | 2432 |
| 167 | 2418 |
| 178 | 2526 |
| 190 | 2483 |
| 201 | 2517 |
| 213 | 2459 |
| 224 | 2475 |
| 236 | 2264 |
| 247 | 2400 |
| 259 | 2271 |
| 270 | 2299 |
| 282 | 2320 |
| 293 | 2306 |
| 305 | 2210 |
| 316 | 2177 |
| 327 | 2223 |
| 339 | 2230 |
| 350 | 2210 |
| 362 | 2115 |
| 374 | 2055 |
| 385 | 2051 |
| 396 | 1975 |

EXAMPLE 5

An alloy containing Ni, Al, Cr and Fe was activated in an aqueous 20 wt.-% NaOH suspension between 100 and 110° C. resulting in an activated Ni catalyst containing 4.07 wt % Al, 0.73% Cr and 0.28 wt % Fe that was doped with an aqueous solution of an ammonium molybdate salt to the final Mo content of 0.1 wt % Mo. This catalyst had an APS value of 23 µm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 5.0. The individual takovite-to-nickel ratios of the x-ray peaks at 12, 24, 35, 40 and 47 °2 theta can be seen in table 2. As described in application example 1, 300 milligrams of this catalyst were used for the pulse hydrogenation of dinitrotoluene to toluenediamine. The selectivity of this reaction was greater than 99.5% toluenediamine and the activity data points are given below in table 10 and graph 2

TABLE 10

The dinitrotoluene hydrogenation data for example 5.

| grams TDA yielded per gram of catalyst | Hydrogenation Activity ml H$_2$ per minute per gram of catalyst |
|---|---|
| 11 | 3004 |
| 21 | 3413 |
| 29 | 3020 |
| 39 | 3130 |
| 49 | 3724 |
| 60 | 3407 |
| 71 | 3603 |

TABLE 10-continued

The dinitrotoluene hydrogenation data for example 5.

| grams TDA yielded per gram of catalyst | Hydrogenation Activity ml H$_2$ per minute per gram of catalyst |
|---|---|
| 82 | 3761 |
| 93 | 3983 |
| 105 | 3983 |
| 116 | 3815 |
| 128 | 3652 |
| 139 | 3876 |
| 151 | 3679 |
| 162 | 3564 |
| 174 | 3547 |
| 185 | 3876 |
| 197 | 3356 |
| 208 | 3795 |
| 220 | 3860 |
| 231 | 3417 |
| 243 | 3582 |
| 254 | 3519 |
| 266 | 3553 |
| 277 | 3588 |
| 289 | 3326 |
| 301 | 3433 |
| 312 | 3403 |
| 323 | 3502 |
| 335 | 3311 |
| 346 | 3310 |
| 358 | 3162 |
| 369 | 3170 |
| 381 | 2968 |
| 393 | 3091 |
| 404 | 3028 |

EXAMPLE 6

An alloy containing Ni, Al, Cr and Fe was activated in an aqueous 20 wt.-% NaOH suspension between 100 and 110° C. resulting in an activated Ni catalyst containing 4.1 wt % Al, 0.72% Cr and 0.28 wt % Fe that was doped with an aqueous solution of CuSO$_4$ to the final Cu content of 0.11 wt % Cu. This catalyst had an APS value of 23 µm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 4.2. The individual takovite-to-nickel ratios of the x-ray peaks at 12, 24, 35, 40 and 47 °2 theta can be seen in table 2. As described in application example 1, 300 milligrams of this catalyst were used for the pulse hydrogenation of dinitrotoluene to toluenediamine except that 300 milligrams instead of 150 milligrams of catalyst was used. The selectivity of this reaction was greater than 99.5% toluenediamine and the activity data points are given below in table 11 and graph 2

TABLE 11

The dinitrotoluene hydrogenation data for example 6.

| grams TDA yielded per gram of catalyst | Hydrogenation Activity ml H$_2$ per minute per gram of catalyst |
|---|---|
| 9 | 2863 |
| 16 | 2891 |
| 24 | 3370 |
| 32 | 3427 |
| 40 | 3399 |
| 49 | 3277 |
| 58 | 3469 |

TABLE 11-continued

The dinitrotoluene hydrogenation data for example 6.

| grams TDA yielded per gram of catalyst | Hydrogenation Activity ml H$_2$ per minute per gram of catalyst |
|---|---|
| 67 | 3619 |
| 77 | 3469 |
| 86 | 3650 |
| 95 | 3347 |
| 105 | 3224 |
| 114 | 3543 |
| 124 | 3257 |
| 133 | 3257 |
| 142 | 3091 |
| 152 | 3075 |
| 161 | 2992 |
| 171 | 3066 |
| 180 | 3045 |
| 189 | 2932 |
| 199 | 2844 |
| 208 | 2792 |
| 218 | 3166 |
| 228 | 2970 |
| 237 | 2985 |
| 246 | 3064 |
| 256 | 2869 |
| 265 | 3097 |
| 275 | 3029 |
| 285 | 2805 |
| 294 | 2983 |
| 304 | 2741 |
| 313 | 2705 |
| 322 | 2792 |
| 332 | 2766 |
| 341 | 2589 |
| 351 | 2927 |
| 361 | 2844 |
| 370 | 2683 |

EXAMPLE 7

An alloy containing Ni, Al, Cr and Fe was activated in an aqueous 20 wt.-% NaOH suspension between 100 and 110° C. resulting in an activated Ni catalyst containing 4.53 wt % Al, 1.51% Cr and 0.29 wt % Fe that was doped with an aqueous solution of an ammonium molybdate salt to the final Mo content of 0.13 wt % Mo. This catalyst had an APS value of 23 µm. This catalyst was used for the batch hydrogenation of nitrobenzene to aniline as described in application example 2. The nitrobenzene hydrogenation activity of this catalyst was found to be 80 ml H$_2$/min/gram of catalyst (please see table 1). As described in application example 1, 300 milligrams of this catalyst were used for the pulse hydrogenation of dinitrotolunene to toluenediamine. The selectivity of this reaction was greater than 99.5% toluenediamine and the activity data points are given below in table 12 and graph 2

TABLE 12

The dinitrotoluene hydrogenation data for example 7.

| grams TDA yielded per gram of catalyst | Hydrogenation Activity ml H$_2$ per minute per gram of catalyst |
|---|---|
| 9 | 3440 |
| 15 | 3046 |
| 20 | 3130 |
| 28 | 3344 |
| 37 | 3602 |
| 46 | 3627 |
| 56 | 3912 |

TABLE 12-continued

The dinitrotoluene hydrogenation data for example 7.

| grams TDA yielded per gram of catalyst | Hydrogenation Activity ml H$_2$ per minute per gram of catalyst |
|---|---|
| 66 | 3888 |
| 76 | 3725 |
| 85 | 3535 |
| 95 | 3471 |
| 105 | 3398 |
| 114 | 3804 |
| 125 | 3575 |
| 134 | 3649 |
| 144 | 3527 |
| 155 | 3490 |
| 164 | 3592 |
| 174 | 3763 |
| 184 | 3548 |
| 194 | 3583 |
| 204 | 3174 |
| 214 | 3202 |
| 223 | 3291 |
| 233 | 3308 |
| 243 | 3344 |
| 253 | 3381 |
| 262 | 3420 |
| 271 | 3382 |
| 281 | 3079 |
| 290 | 3306 |
| 300 | 3119 |
| 309 | 3104 |
| 318 | 2924 |
| 327 | 3168 |
| 337 | 3219 |
| 346 | 3015 |
| 355 | 3071 |
| 365 | 2853 |
| 373 | 2867 |

EXAMPLE 8

An alloy containing Ni, Al and Fe was activated in an aqueous 20 wt.-% NaOH suspension in the presence of a fine Cr powder between 100 and 110° C. resulting in an activated Ni catalyst containing 3.92 wt % Al, 0.42% Cr and 0.22 wt % Fe. This catalyst had an APS value of 20 µm and was tested for the formation of takovite as described in application example 3. The ratio of the sum of the takovite x-ray diffraction peak heights at 12, 24, 35, 40 and 47 °2 theta to the nickel x-ray diffraction peak height at 52 °2 theta was found to be 0.0. The individual takovite-to-nickel ratios of the x-ray peaks at 12, 24, 35, 40 and 47 °2 theta can be seen in table 2.

The results shown in the above examples clearly demonstrate that the present invention is well adapted to carry out the objectives and attain the ends and advantages mentioned as well as those inherent therein. While increasing the Al content of the catalyst enhances its activity, it can also increase the amount of takovite produced during the hydrogenation of nitro-compounds such as dinitrotoluene. Hence in the past, one had to select between either higher activity and the increased presence of takovite, or less catalyst activity (with lower Al contents) and less takovite. Stabilizing the Al in the catalyst by the inventions of this patent will allow the practitioner of nitro-compound hydrogenation to have both high activity and less takovite. Application example 3 describes how we determined the ability of the catalyst to form takovite and the ratio of the sum of takovite °2 theta peak heights to the Ni 52 °2 theta peak height normalizes this measurement with respect to the XRD measured Ni quantity and this value is referred to here as the takovite propensity. To compare the takovite propensities of catalysts containing different Al contents one should then divide the takovite propensity by the wt. % Al to determine the relative amount of Al in the catalyst that is leachable with a amino compounds such as toluenediamine (TDA) to form takovite. Another aspect is the activity of the catalyst. If the catalyst is highly active, one would need less of this catalyst to form the same amount of the desired amine. Hence the most important aspect of the takovite propensity is the relative amount of takovite formed with respect to catalyst activity and the wt. % Al. Since the dinitrotoluene hydrogenation experiments measured here go to a minimum of ~350 grams of toluenediamine produced per gram of catalyst, we took the average activity up to 350 grams of toluenediamine per gram of catalyst as the standard comparison for our catalysts and this together with the relative amount of takovite formed with respect to activity and Al content are listed in table 13. One can see from the data that the proper selection of doping methods and doping elements can surprisingly lead to a catalyst that has a high activity and forms a low amount of takovite with respect to activity and Al content.

TABLE 13

The comparison of takovite formation with respect to Al content and pulse dinitrotoluene hydrogenation activity.

| Catalyst | Doping elements | APS μm | Average Activity to 350 g TDA per g cat | wt. % Al | Sum Takovite:Ni | Ratio of Takovite:Ni to wt. % Al | Relative Activity to CE2 | Relative amount of Takovite with respect to wt % Al and Activity |
|---|---|---|---|---|---|---|---|---|
| CE1 | Cr, Fe | 35 | 379 | 8.8 | 50.2 | 5.70 | 0.24 | 24.08 |
| CE2 | Fe | 28 | 1599 | 4 | 4.7 | 1.17 | 1.00 | 1.17 |
| CE3 | Cr, Fe | 29 | 2709 | 6.3 | 20.9 | 3.33 | 1.69 | 1.96 |
| E1 | Cr, Fe | 29 | 2740 | 3.43 | 2.6 | 0.76 | 1.71 | 0.44 |
| E2 | Fe, Cu | 29 | 1769 | 3.46 | 0.0 | 0.00 | 1.11 | 0.00 |
| E3 | Fe, Mo | 17 | 2528 | 3.87 | 2.5 | 0.65 | 1.58 | 0.41 |
| E4 | Fe, Cu | 20 | 2413 | 3.81 | 0.0 | 0.00 | 1.51 | 0.00 |
| E5 | Cr, Fe, Mo | 23 | 3548 | 4.07 | 5.0 | 1.23 | 2.22 | 0.55 |
| E6 | Cr, Fe, Cu | 23 | 3089 | 4.1 | 4.2 | 1.02 | 1.93 | 0.53 |

While modification may be made by those skilled in the art, such modifications are encompassed within the spirit of the present invention as defined by the disclosure and the claims.

The invention claimed is:

1. An activated powder catalyst comprising:
a) a Ni/Al alloy comprising one or more doping elements selected from the group consisting of Mg, V, Cr, Mo, Fe, Co, Pd and Pt, said doping elements having been added before activation, and wherein said activated powder catalyst comprises 0.01 wt % to 5 wt % of each doping element; and
b) Cu or Mo adsorbed on the surface of the activated powder catalyst, said Cu or Mo having been adsorbed after activation, and wherein said activated powder catalyst comprises 0.01 wt % to 5 wt % of said Cu or Mo;
wherein said activated powder catalyst comprises 0.05 wt % to 10 wt % Al.

2. The activated powder catalyst of claim 1, wherein said Ni/Al alloy comprises one or more doping elements selected from the group consisting of: Cr, Mo or Fe, said doping elements having been added before activation, and Cu is adsorbed on the surface of the activated powder catalyst, said Cu having been adsorbed after activation.

3. The activated powder catalyst of claim 1, wherein said Ni/Al alloy comprises one or more doping elements selected from the group consisting of: Mo, Cr or Fe, said doping elements having been added before activation and Mo is adsorbed on the surface of the activated powder catalyst, said Mo having been adsorbed after activation.

4. The activated powder catalyst of claim 1, wherein said Ni/Al alloy comprises the doping elements Cr and Fe, said doping elements having been added before activation and Cu or Mo are adsorbed on the surface of the activated powder catalyst, said Cu or Mo having been adsorbed after activation.

5. A method for the hydrogenation of a nitro-compound, comprising reacting said nitro compound with hydrogen in the presence of the activated powder catalyst of claim 1.

6. The method of claim 5, wherein said nitro-compound is a nitrated aromatic.

7. The method of claim 5, wherein said hydrogenation of said nitro-compound is carried out continuously.

8. The activated powder catalyst of claim 1, wherein Mo is adsorbed on the surface of the activated powder catalyst, said Mo having been adsorbed after activation.

9. The activated powder catalyst of claim 1, wherein Cu is adsorbed on the surface of the activated powder catalyst, said Cu having been adsorbed after activation.

10. The activated powder catalyst of claim 1, wherein said activated powder catalyst comprises 0.01 to 1.9 wt % of Fe.

11. The activated powder catalyst of claim 1, wherein said activated powder catalyst comprises 0.01 to 2.4 wt % Cr.

12. The activated powder catalyst of claim 1, wherein said activated powder catalyst comprises 0.01 to 1.9 wt % of Fe and 0.01 to 2.4 wt. % Cr.

13. The method of claim 5, wherein the Ni/Al alloy in said activated powder catalyst comprises one or more doping elements selected from the group consisting of Cr, Mo, or Fe, said doping elements having been added before activation, and Cu is adsorbed on the surface of the activated powder catalyst, said Cu having been adsorbed after activation.

14. The method of claim 5, wherein the Ni/Al alloy in said activated powder catalyst comprises one or more doping elements selected from the group consisting of Cr, Mo, or Fe, said doping elements having been added before activation, and Mo is adsorbed on the surface of the activated powder catalyst, said Mo having been adsorbed after activation.

15. The method of claim 5, wherein the Ni/Al alloy in said activated powder catalyst comprises the doping elements Cr and Fe, said doping elements having been added before activation, and Cu or Mo is adsorbed on the surface of the activated powder catalyst, said Cu or Mo having been adsorbed after activation.

16. The method of claim 5, wherein Mo is adsorbed on the surface of the activated powder catalyst, said Mo having been adsorbed after activation.

17. The method of claim 5, wherein Cu is adsorbed on the surface of the activated powder catalyst, said Cu having been adsorbed after activation.

18. The method of claim 5, wherein said activated powder catalyst comprises 0.01 to 1.9 wt % Fe.

19. The method of claim 5, wherein said activated powder catalyst comprises 0.01 to 2.4 wt % Cr.

20. The method of claim 5, wherein said activated powder catalyst contains 0.01 to 1.9 wt % Fe and between 0.01 and 2.4 wt % Cr.

* * * * *